United States Patent

Steinel, Jr.

[11] Patent Number: 6,148,143
[45] Date of Patent: Nov. 14, 2000

[54] ELECTRIC DEVICE FOR EVAPORATING ACTIVE SUBSTANCES

[75] Inventor: Heinrich Wolfgang Steinel, Jr., Bad Woerishofen, Germany

[73] Assignee: Steinel GmbH & Co. KG, Herzebrock-Clarholz, Germany

[21] Appl. No.: 09/242,498

[22] PCT Filed: Aug. 27, 1997

[86] PCT No.: PCT/EP97/04676

§ 371 Date: Dec. 13, 1999

§ 102(e) Date: Dec. 13, 1999

[87] PCT Pub. No.: WO98/09661

PCT Pub. Date: Mar. 12, 1998

[30] Foreign Application Priority Data

Sep. 4, 1996 [DE] Germany .............................. 96114199

[51] Int. Cl.⁷ .............................. A61M 16/00; H05B 3/06
[52] U.S. Cl. .............................. 392/390; 219/536
[58] Field of Search ..................... 392/386, 390, 392/391, 392, 394, 395; 261/DIG. 65, 142; 219/536, 537, 542, 544; 338/226, 22 R, 23

[56] References Cited

U.S. PATENT DOCUMENTS 4,728,779  3/1988  Kotani et al. ........................ 338/22 R
4,874,924  10/1989  Yamamoto et al. .................... 392/395
5,556,192  9/1996  Wang ................................... 362/276
5,647,053  7/1997  Schroeder et al. .................... 392/390
5,940,577  8/1999  Steinel ................................ 392/395

FOREIGN PATENT DOCUMENTS 0 695 553   2/1996   European Pat. Off. .
0 696 457   2/1996   European Pat. Off. .
16 65 063   10/1970  Germany .

*Primary Examiner*—Sang Paik
*Attorney, Agent, or Firm*—Darby & Darby

[57] ABSTRACT

An electric device for evaporating substances, such as perfumes or the like, including a housing which is adapted to have inserted therein a receptacle containing the substance in question. The device has an electric circuit supported in the housing and formed of two circuit components which are placed one on top of the other and between which a PTC element is arranged. Each of the circuit components is formed of an injection molded part and a stamped sheet metal component embedded therein. The circuit components are coupled to one another mechanically and electrically by an integrally formed stamped sheet metal component and one circuit component is folded onto the other when the device is being assembled.

6 Claims, 3 Drawing Sheets

ELECTRIC DEVICE FOR EVAPORATING ACTIVE SUBSTANCES

BACKGROUND OF THE INVENTION

The present invention refers to an electric device for evaporating substances, perfumes or the like, according to the generic clause of patent claim 1.

Such devices have become known from EP 686 457 A1 and EP 695 553 A1.

The device described in these two applications comprises a two-part electric circuit consisting of two stamped sheet metal components embedded in plastic material by means of injection moulding and placed one on top of the other. When this device is being produced, an integral stamped sheet metal component is embedded in plastic material by means of injection moulding and separated into two parts before it is mounted. Furthermore, projecting parts of the stamped sheet metal component must be cut off and bending operations are required so as to be able to establish an electric connection between the two superimposed parts. Finally, a mechanical connection must be established between the circuit components, e.g. by means of a pushed-on metal clip. These additional operating steps constitute a substantial cost factor in mass production and especially the fact that one part has to be placed on top of the other requires either highly complicated positioning means or expensive manual labour.

It is therefore the object of the present invention to further develop a device of the type mentioned at the beginning in such a way that it can be produced as simply as possible and at the lowest possible price.

BRIEF DESCRIPTION OF THE INVENTION

In the electric device according to the present invention the stacked circuit components are coupled mechanically as well as electrically by means of an integrally formed stamped sheet metal component. When the device is being mounted, one circuit component is simply folded onto the other, the mechanical coupling uniting the circuit components like a hinge. Hence, it is not necessary to take hold of two separate circuit components and to position them relative to one another, as has to be done in the case of the prior art. Due to the mechanical coupling, the additional clip required for keeping the circuit components together is no longer necessary either.

The integrally formed stamped sheet metal component also provides an electric connection between the two circuit components; said electric connection required additional bending operations in the prior art.

It follows that the device according to the present invention consists of a smaller number of parts, it has a less complicated structural design and it can be assembled much more easily; this will result in substantial advantages with regard to production costs.

In accordance with a preferred embodiment, at least one injection moulded part has formed therein openings for accommodating discrete electric components, whereby the circuit can be equipped more easily.

In particular, it will be advantageous when the openings provided in one injection moulded part have associated therewith complementary protruding retaining projections which are provided on the other injection moulded part, since this will have the effect that, when one circuit component is folded onto the other, the connecting wires of the components will clampingly be held between said retaining projections and the stamped sheet metal component. It follows that, when the circuit is being equipped with electric components, neither soldering nor spot welding is required for providing an electrically conductive connection between the connecting wires of the components and the stamped sheet metal component.

According to a preferred embodiment, at least one injection moulded part has formed therein openings which are adapted to be brought into locking engagement with complementary retaining projections on the other injection moulded part. This will facilitate exact positioning of the two circuit components and provide a snap connection which is easy to establish.

In accordance with a further preferred embodiment, the device is provided with electric connecting pins extending into the interior of the housing. For providing a positive engagement with said connecting pins, one injection moulded part has formed therein complementary reception openings. The electric circuit can directly be connected to a voltage supply in this way, without using any pigtail leads: this will make the production of the device less complicated and less expensive.

BRIEF DESCRIPTION OF THE DRAWINGS

A preferred embodiment of the present invention will now be described making reference to the accompanying figures, in which.

DETAILED DESCRIPTION OF THE INVENTION

Figure 1:
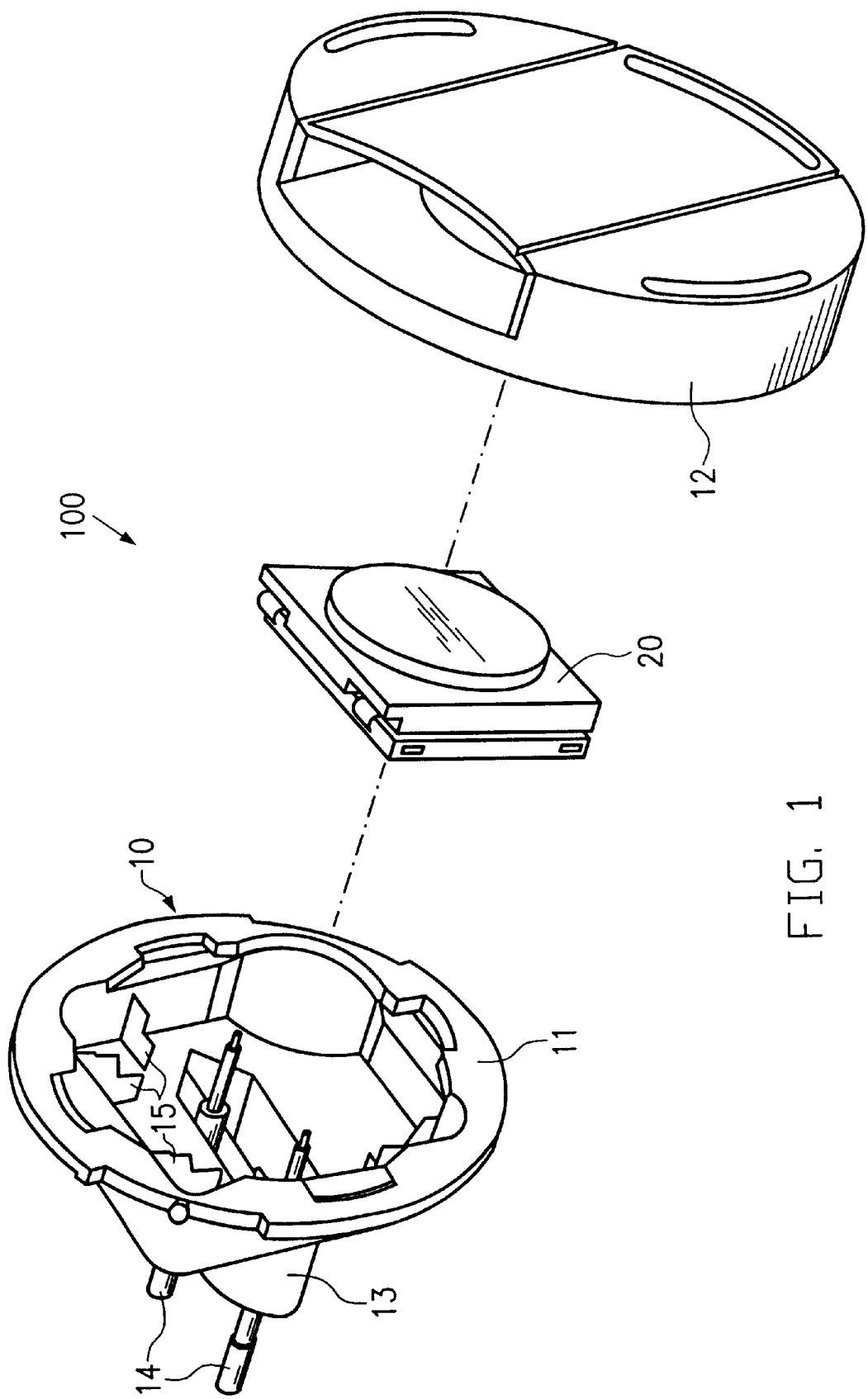
FIG. 1 shows a perspective exploded view of the device according to the present invention.

Making reference to FIG. 1, the electric device 100 consists of a two-part housing 10 and an electric circuit 20 supported therein. The housing comprises a connecting part 11 and a cover 12 which is adapted to be fastened thereto.

The connecting part 11 includes a projecting connector base 13 which is provided at the rear outer surface thereof and from which two connecting pins 14 project. The connector base and the connecting pins are shaped such that they are suitable to be connected to a standardized wall socket or table socket. On the inner side of the housing of the connecting part retaining webs 15 are formed, which serve to retain the electric circuit 20.

The cover 12 is adapted to be secured to the connecting part by means of detent projections and the circumferential edge thereof is provided with an opening for inserting a tray, not shown, consisting of plastic or of metal, e.g. aluminium, into a pocket which is formed in said cover and which contains the substance to be evaporated. The cover is also provided with ventilation openings for permitting air to circulate through the interior of the housing.

Figure 2:
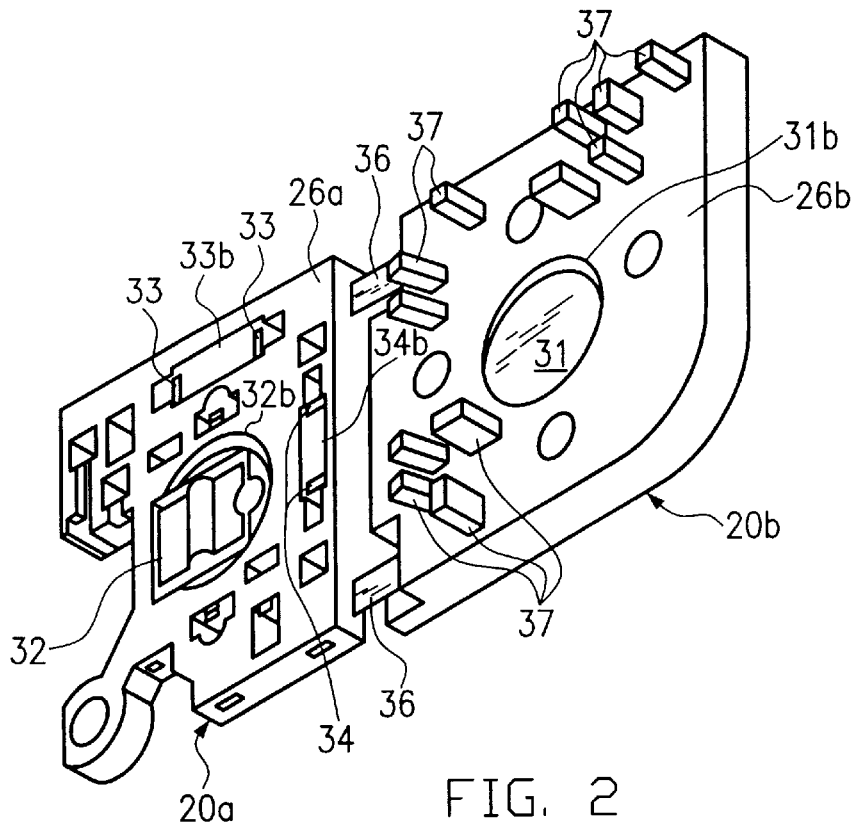
FIG. 2 shows a perspective view of the electric circuit of the device according to the present invention as shown in FIG. 1, prior to the mounting operation.

In the following, reference is made to FIG. 2 which shows in detail the electric circuit 20 before it is mounted.

The circuit consists of two circuit components 20a, 20b which are produced by embedding the lower side and the upper side of an integral stamped sheet metal component in plastic material by injection moulding. The stamped sheet metal component is already provided with all electric current paths, connection contacts and electrodes. The material used for embedding the stamped sheet metal component is a plastic insulation material, which is applied in several layers, if necessary, and which increases the rigidity of said stamped sheet metal component. This plastic insulation material is applied by injection moulding in such a way that two separate injection moulded parts of plastic material 26a, 26b are formed, which are held together through two free webs 36 of the integral stamped sheet metal component.

Figure 3:
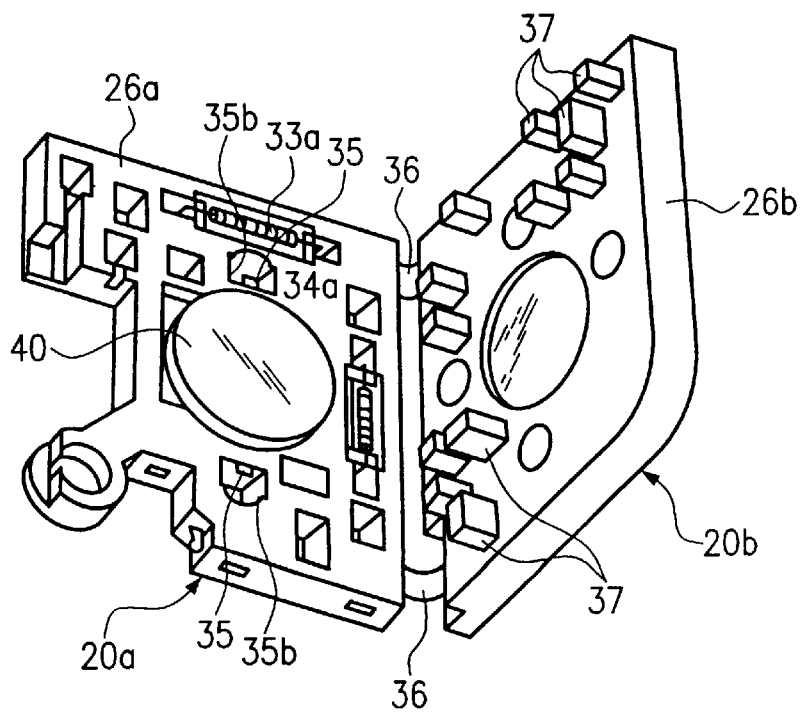
FIG. 3 shows a perspective view of the electric circuit according to FIG. 2 during the mounting operation.

The stamped sheet metal component comprises a first electrode 31 and a second electrode 32 with a resilient tongue which is cut free and used for a PTC heating element 40 (FIG. 3). In addition, the stamped sheet metal component 25 comprises connection contacts 33, 34 for electric resistors 33a and for an indicator lamp 34a. Finally, connection lugs 35 are arranged on both sides of the electrode 32, said connection lugs contacting the connecting pins 14 in the assembled condition of the device so that the circuit can be supplied with electric voltage.

The above-mentioned connections and electrodes are located in respective openings 31b to 35b associated therewith, which are formed in the injection moulded part 26a and which define reception means for the electric components of the fully mounted circuit.

The openings of one injection moulded part 26a have associated therewith retaining projections 37 of rectangular or square cross-section on the other injection moulded part 26b.

Figure 4:
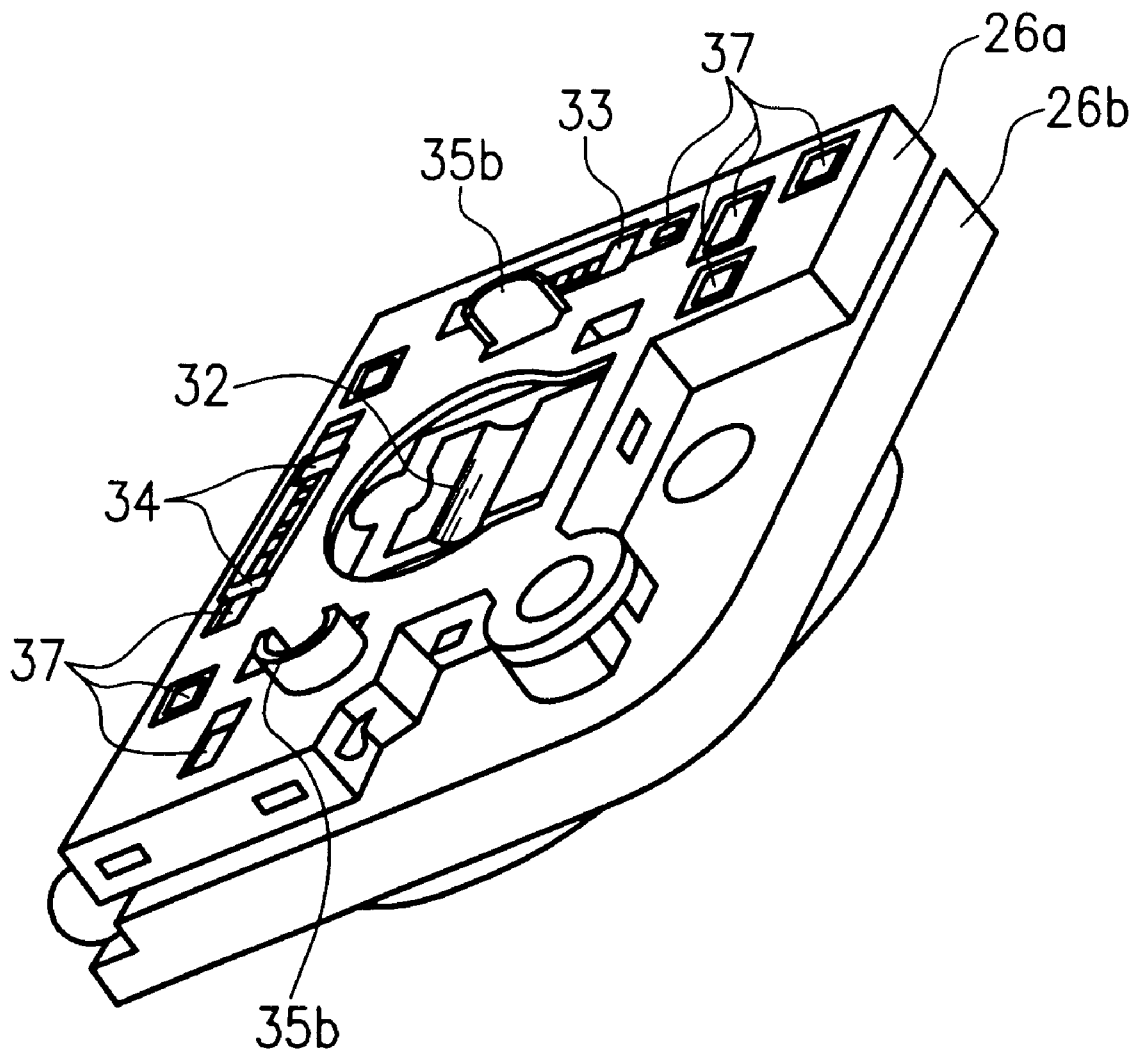
FIG. 4 shows a fully mounted and equipped electric circuit of the device according to the present invention.

FIG. 3 and 4 show the steps for producing a fully equipped electric circuit 20. It can be seen that the webs 36 define a kind of mechanical hinge, the first injection moulded part 26a being folded onto the second injection moulded part 26b when the electric components have been inserted. The webs 36 will be bent by 180° when the injection moulded parts are folded onto each other. In the closed condition, the openings 31b to 35b engage the complementary retaining projections 37 for connecting the two injection moulded parts. If desired, the two injection moulded parts can be brought into fixed, locking engagement with each other by providing detent projections on said retaining projections 37.

As can be seen from FIG. 4, the retaining projections 37 having associated therewith openings 31b to 35b, in which an electric component is accommodated, will bend the horizontally extending connecting wires of components 33a, 34a by 90° when the injection moulded parts are folded onto each other. The connection contacts 33, 34 of the stamped sheet metal component cooperate with the projections 37 in such a way that the connecting wires of the electric components are held therebetween in a clamped condition. This has the effect that a reliable electric connection is established between the connection contacts and the connecting wires of said electric components.

The fully assembled circuit 20 is inserted in the connecting part 11, the connecting pins 14 coming into positive engagement with the openings 35b, in which the connection lugs 35 are located, in the course of this process. Finally, the cover 12 is attached to the connecting part and rotated until it is locked in position.

The device can additionally be provided with a toggle switch, which is not shown, so as to permit an interruption of the voltage supply also without removing the device from the socket. In this case, the toggle switch is e.g. secured to the electric circuit and can be operated from outside through an opening provided in the housing. In addition, the device may be equipped with a timer interrupting the voltage supply after a fixedly predetermined or adjustable period of time and guaranteeing in this way that the device is switched off reliably.

What is claimed is:

1. An electric device for evaporating substances, such as perfumes or the like, comprising:

a housing which is adapted to have inserted therein a receptacle containing the substance, and an electric circuit supported in said housing formed of two circuit components placed one on top of the other and between which a PTC element is arranged, each of said circuit components comprising an injection molded part and a stamped sheet metal component embedded therein, said circuit components being coupled to one another mechanically and electrically by an integrally formed stamped sheet metal component, one circuit component being folded onto the other when the device is being assembled.

2. An electric device according to claim 1, wherein at least one injection molded part has formed therein openings for accommodating discrete electric components.

3. An electric device according to claim 2, wherein the openings provided in said one injection molded part have associated therewith complementary protruding retaining projections on the other injection molded part and which clampingly hold connecting wires of the components between them and the stamped sheet metal component when one circuit component is folded onto the other.

4. An electric device according to claim 1, wherein at least one injection molded part has formed therein openings which are adapted to be brought into locking engagement with complementary retaining projections of the other injection molded part.

5. An electric device according to claim 1, wherein one injection molded part has formed therein reception openings for positive engagement with electric connecting pins.

6. An electric device according to claim 1, wherein the circuit components are coupled to one another via two parallel, exposed webs of the stamped sheet metal component.

* * * * *